United States Patent [19]
Sugo et al.

[11] Patent Number: 5,876,348
[45] Date of Patent: Mar. 2, 1999

[54] BLOOD PRESSURE MONITORING APPARATUS

[75] Inventors: Yoshihiro Sugo; Takeshi Sohma; Hiromitsu Kasuya; Rie Tanaka, all of Tokyo, Japan

[73] Assignee: Nihon Kohden Corporation, Tokyo, Japan

[21] Appl. No.: 993,562

[22] Filed: Dec. 18, 1997

[30] Foreign Application Priority Data

Jan. 6, 1997 [JP] Japan ................................. 9-000205

[51] Int. Cl.$^6$ ....................................................... A61B 5/02
[52] U.S. Cl. .......................... 600/490; 600/490; 600/485; 600/500; 600/494
[58] Field of Search .................................. 600/500, 494, 600/495, 490, 485, 493

[56] References Cited

U.S. PATENT DOCUMENTS

| | | | |
|---|---|---|---|
| 5,033,472 | 7/1991 | Sato et al. ................................. | 128/691 |
| 5,564,427 | 10/1996 | Aso et al. ................................. | 128/681 |
| 5,603,329 | 2/1997 | Hosaka et al. ............................ | 128/680 |
| 5,649,543 | 7/1997 | Hosaka et al. ............................ | 128/681 |
| 5,743,856 | 4/1998 | Oka et al. ................................. | 600/485 |
| 5,752,913 | 5/1998 | Oka .......................................... | 600/485 |

*Primary Examiner*—Robert L. Nasser
*Assistant Examiner*—Michael Astorino
*Attorney, Agent, or Firm*—Sughrue, Mion, Zinn, Macpeak & Seas, PLLC

[57] ABSTRACT

During a noninvasive blood pressure measurement using a cuff 2, a pulse wave propagation time T1 from the appearance of the peak value of an R wave in an electrocardiogram (ECG) waveform to the appearance of the bottom value of a pulse wave is counted, and a blood pressure value BP1 is calculated from a count result T1 and parameters α, β specific to a subject obtained during a pulse wave propagation time calibration. Then, the absolute value of a difference between the blood pressure value BP1 and a blood pressure value NIBP1 obtained by the noninvasive blood pressure measurement using the cuff 2 is calculated, and it is indeed whether or not the calculated absolute value is within a predetermined threshold_BP. If the absolute value is judged to exceed the threshold_BP, then blood pressure is measured again noninvasively using the cuff 2, and a blood pressure value NIBP1'obtained from such repeated measurement is displayed on a display 22.

4 Claims, 3 Drawing Sheets

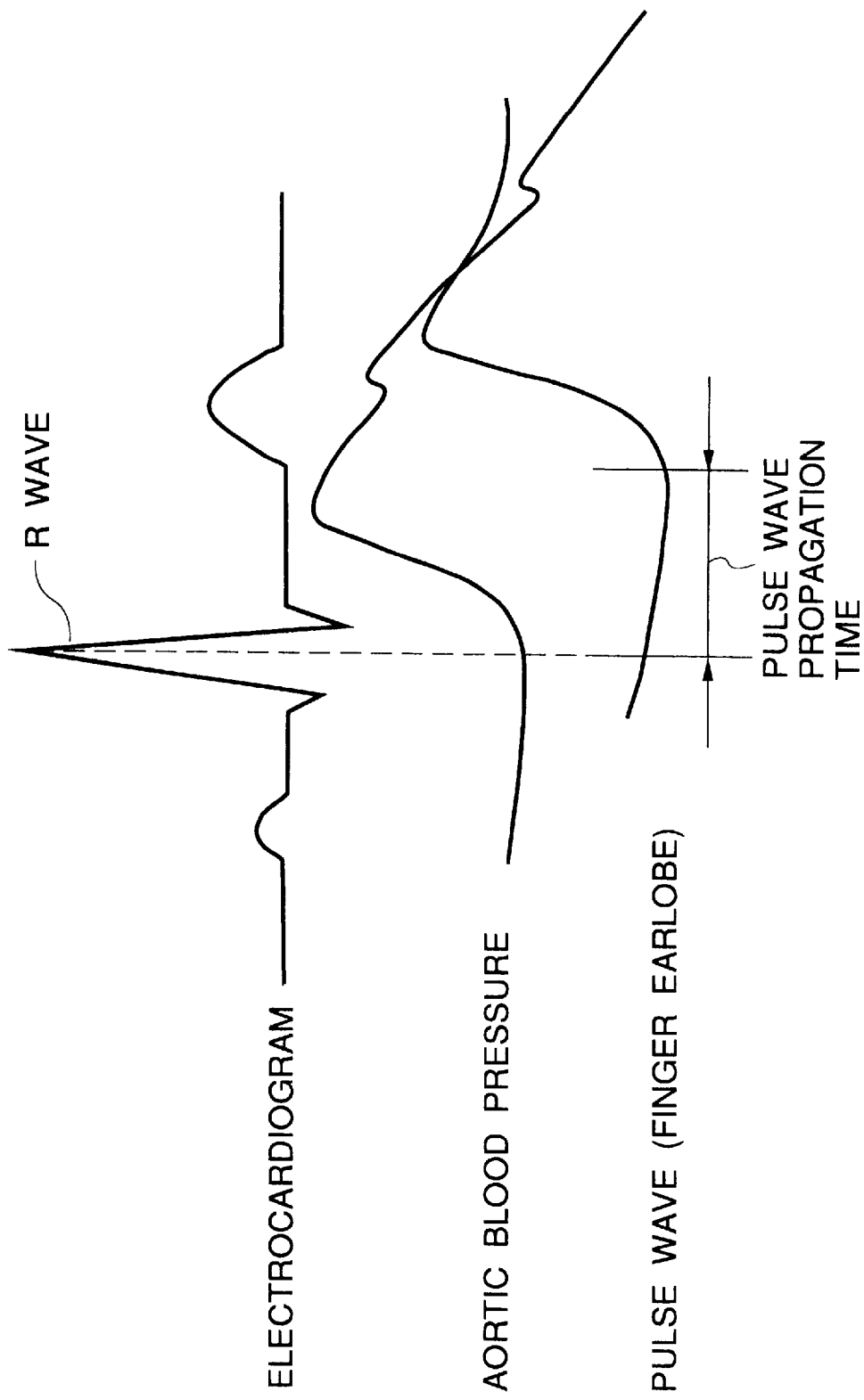

BLOOD PRESSURE MONITORING APPARATUS

BACKGROUND OF THE INVENTION

1. Field of the invention

The present invention relates to blood pressure monitoring apparatuses to be applied to such fields as requiring continuous blood pressure monitoring for subjects to be treated in operating rooms, intensive care units, emergency treatment rooms, extracorporeal dialysis rooms, and the like. More particularly, the present invention is directed to a blood pressure monitoring apparatus that monitors biological data such as electrocardiograms (ECG), pulse waves, and blood pressure.

2. Related art

A blood pressure monitoring apparatus that monitors biological data such as ECGs, pulse waves, in addition to blood pressure, has heretofore been known. This type of monitoring is generally called "vital sign monitor".

This blood pressure monitoring apparatus has a cuff to be attached to a brachium, a finger, or the like of a subject, a pulse oximeter probe, and ECG electrodes to be attached to the chest of the subject. The blood pressure monitoring apparatus measures blood pressure, ECGs, and pulse waves by attaching these members onto the subject, and displays the measured results. In this case, a noninvasive blood pressure measurement based on cuff pressure is made at a predetermined interval.

By the way, such conventional blood pressure monitoring apparatus has addressed the following problems.

In a noninvasive blood pressure measurement based on cuff pressure, when a subject moves or a medical stuff member touches the cuff during the measurement, measured values may, in some cases, become abnormal values, and the conventional blood pressure monitoring apparatus uses such abnormal values in computation, which has imposed the problem that unnecessary alarming has to be given or that post-measurement analyses cannot be done smoothly.

Further, even if such abnormality has been found, a re-measurement must be made and such re-measurement must be started manually, which in turn has made operability not so satisfactory.

SUMMARY OF THE INVENTION

The object of the present invention is, therefore, to provide a blood pressure monitoring apparatus that not only can detect an abnormality in the result of a noninvasive blood pressure measurement based on cuff pressure but also can automatically make a re-measurement when an abnormality has been found.

According to the present invention, a blood pressure monitoring apparatus that includes: blood pressure measuring means for measuring blood pressure using a cuff; time interval detection reference point detecting means for detecting a time interval detection reference point on a pulse wave at an aorta of a body; pulse wave detecting means for detecting a pulse wave at peripheral blood vessels appearing with a time delay with respect to the pulse wave at the aorta; pulse wave propagation time counting means for counting a pulse wave propagation time based on detected outputs from the time interval detection reference point detecting means and the pulse wave detecting means; and control means for judging whether or not a blood pressure value measured by the blood pressure measuring means is an abnormal value based on a fluctuating condition observed on the blood pressure value measured by the blood pressure measuring means and a fluctuating condition observed on a pulse wave propagation time counted by the pulse wave propagation time counting means at the time the blood pressure value has been measured, and measuring blood pressure again by controlling the blood pressure measuring means when the blood pressure value has been judged to be an abnormal value.

According to the present invention, a blood pressure monitoring apparatus includes: blood pressure measuring means for measuring blood pressure using a cuff; threshold storage means for storing a threshold serving as a reference for blood pressure re-measurement using the cuff, the threshold being inputted from an external source; time interval detection reference point detecting means for detecting a time interval detection reference point on a pulse wave at an aorta of a body; pulse wave detecting means for detecting a pulse wave at peripheral blood vessels appearing with a time delay with respect to the pulse wave at the aorta; pulse wave propagation time counting means for counting a pulse wave propagation time based on detected outputs from the time interval detection reference point detecting means and the pulse wave detecting means; calculating means for calculating a blood pressure value based on a pulse wave propagation time counted by the pulse wave propagation time counting means at the time the blood pressure measurement has been made by the blood pressure measuring means; and control means for judging whether or not an absolute value of a difference between a blood pressure value measured by the blood pressure measuring means and a blood pressure value calculated by the calculating means at the time the blood pressure value has been measured exceeds the threshold stored in the threshold storage means, and measuring blood pressure again by controlling the blood pressure measuring means when the absolute value of the difference has been judged to exceed the threshold.

BRIEF DESCRIPTION OF THE DRAWINGS

FIG. 3 is a waveform diagram illustrative of a pulse wave propagation time.

DETAILED DESCRIPTION OF THE PREFERRED EMBODIMENTS

Figure 1:
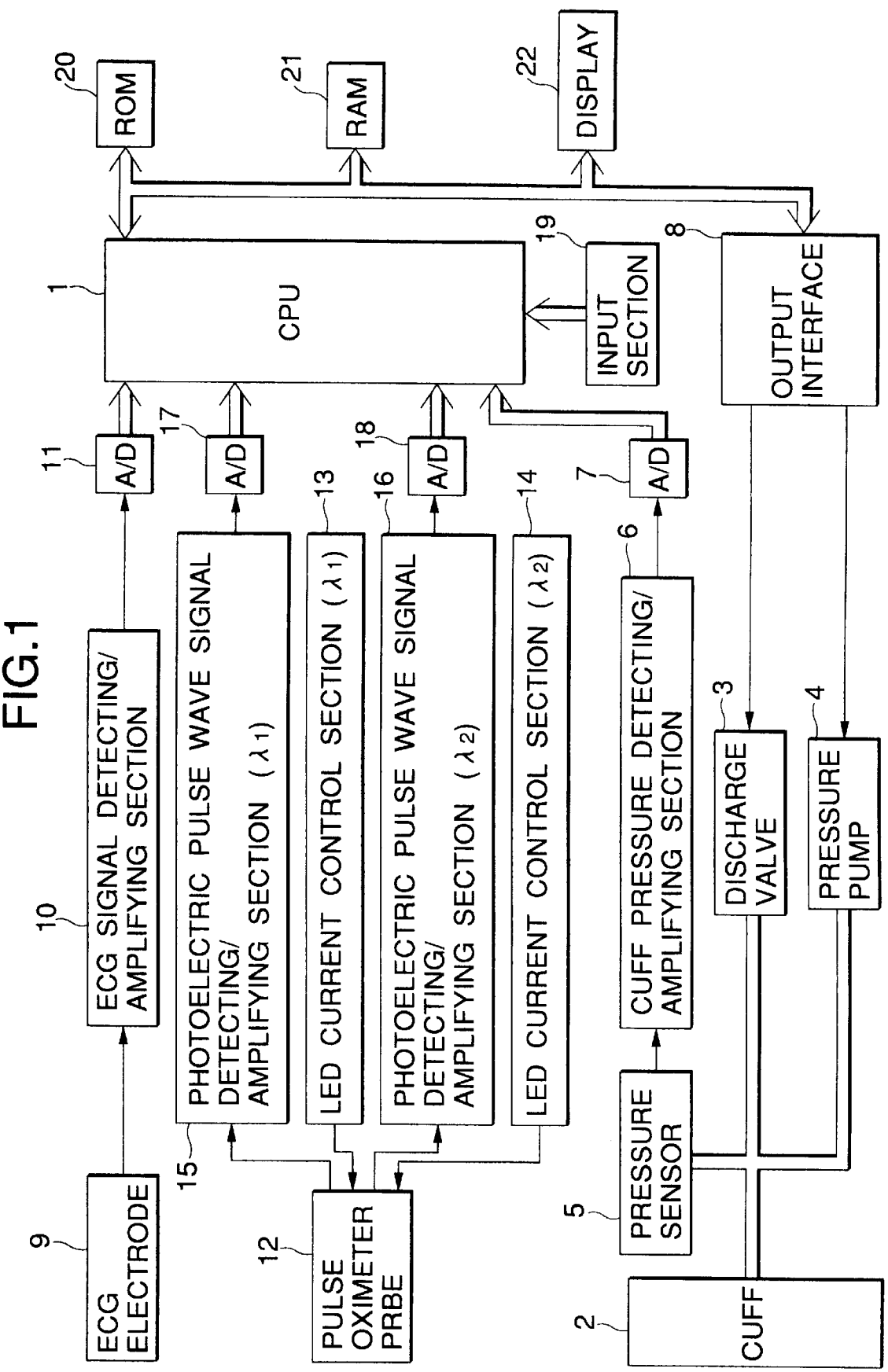
FIG. 1 is a block diagram showing a configuration of a blood pressure monitoring apparatus, which is a mode of embodiment of the present invention.

The basic concept of the present invention will hereunder be described.

Noninvasive blood pressure measurements can be made by a method of using pulse wave propagation time in addition to the aforementioned method of using a cuff. The principle of the blood pressure measurement based on the pulse wave propagation time is as follows.

As shown in FIG. 3, a bottom value of a pulse wave on the side of peripheral blood vessels such as a finger or an ear appears with a delay with respect to a bottom value of an aortic pulse wave. This delay time is the pulse wave propagation time. In this case, the pulse wave propagation time equals a time from the appearance of the top value of an R wave to the appearance of the bottom value of a pulse wave on the side of peripheral blood vessels, taking the R wave of an ECG waveform as a reference.

Blood pressure measurement using the pulse wave propagation time must be calibrated by measuring blood pressure through other means, e.g., using a cuff and referring to the measured results. If, e.g., blood pressure is increased after the calibration, the propagation time is shortened. Therefore, a blood pressure value can be obtained by making a correction based on a time difference between such shortened pulse wave propagation time and a pulse wave propagation time obtained during calibration.

On the other hand, the blood pressure value can be obtained from the following equation as well.

$$P = \alpha T + \beta$$

where T is the pulse wave propagation time; and α, β are the parameters specific to a subject. The parameters α, β specific to a subject can be calculated at the time of calibrating the pulse wave propagation time.

In a pulse wave propagation time calibration, both blood pressure and pulse wave propagation time are measured when a subject is, e.g., at rest and in exercise, respectively.

Here, assuming that the blood pressure value and the pulse wave propagation time at the time the subject is at rest are P1, T1 and that those at the time the subject is in exercise are P2, T2, then the blood pressure values P1, P2 are given, e.g., as follows.

$$P1 = \alpha T1 + \beta \qquad (1)$$

$$P2 = \alpha T2 + \beta \qquad (2)$$

Therefore, by measuring P1, T1, P2, T2, the parameters α, β can be calculated from the above two equations. Once α, β have been calculated, the blood pressure values of the subject can thereafter be measured only by measuring the pulse wave propagation time. It may be noted that in measuring two different blood pressure values, the measuring timings are not limited to such timings at which the subject is at rest and in exercise as long as measuring timings are such as to allow two different blood pressure values to be picked up.

Since a blood pressure value can be obtained from both an ECG and a pulse wave as described above, whether or not a blood pressure value measured in a noninvasive blood pressure measurement is abnormal can be judged based not only on a time difference between the ECG and a pulse wave obtained by a pulse oximeter in a conventional blood pressure monitoring apparatus but also on blood pressure value fluctuations in a noninvasive blood pressure measurement based on cuff pressure. If the blood pressure value is judged to be abnormal, blood pressure may be measured again.

A blood pressure monitoring apparatus, which is a mode of embodiment of the present invention will now be described with reference to the drawings.

A. Configuration of the blood pressure monitoring apparatus

FIG. 1 is a block diagram showing a configuration of the blood pressure monitoring apparatus, which is the mode of embodiment of the present invention. In FIG. 1, a cuff 2 is used to measure blood pressure and designed to be attached to a brachium or a finger of a subject. The inside of the cuff 2 is opened or closed with respect to the atmosphere by a discharge valve 3, and the cuff 2 is supplied with air by a pressure pump 4. Cuff pressure is measured by a pressure sensor 5. The output of the pressure sensor 5 is detected and amplified by a cuff pressure detecting/amplifying section 6. The output of the cuff pressure detecting/amplifying section 6 is converted into a digital signal by an A/D converter 7, and the converted digital signal is thereafter received by a CPU (central processing unit) 1. The CPU 1, the discharge valve 3, and the pressure pump 4 are interconnected through an output interface 8.

Electrocardiogram (ECG) electrodes 9 are used to measure an ECG signal and designed to be attached to the chest or the like of a subject. An ECG signal detecting/amplifying section 10 detects an ECG signal of a subject with the ECG electrodes 9 and amplifies and outputs the detected ECG signal. The output of the ECG signal detecting/amplifying section 10 is converted into a digital signal by an A/D converter 11, and the converted digital signal is thereafter received by the CPU 1. A pulse oximeter probe 12 is used to measure the content of oxygen dissolved in blood and designed to be attached to a finger or the like of a subject.

The pulse oximeter probe 12 includes: an LED (light-emitting diode) that outputs light with a wavelength of λ1 in which an absorbance of deoxyhemoglobin is greatly different from that of an oxyhemoglobin; an LED (light-emitting diode) that outputs light with a wavelength of λ2 in which an absorbance of deoxyhemoglobin is approximately equal to that of oxyhemoglobin; and a phototransistor that detects light from the LED that outputs the light whose wavelength is λ1 and the light from the LED that outputs the light whose wavelength is λ2. In this case, the two LEDs and the phototransistor are disposed so as to confront one another at an equal interval in commensurate with the size of a measuring region of a subject.

An LED current control section 13 controls current that is caused to flow to the LED that outputs the light whose wavelength is λ1 of the pulse oximeter probe 12, and an LED current control section 14 controls current that is caused to flow to the LED that outputs the light whose wavelength is λ2 of the pulse oximeter probe 12. A photoelectric pulse wave signal detecting/amplifying section 15 detects a pulse signal from a phototransistor output, and amplifies and outputs the detected signal. The output of the photoelectric pulse wave signal detecting/amplifying section 15 is converted into a digital signal by an A/D converter 17, and the converted digital signal is thereafter received by the CPU 1.

A photoelectric pulse wave signal detecting/amplifying section 16 detects a pulse wave signal from a phototransistor output, and amplifies and outputs the detected signal. The output of the photoelectric pulse wave signal detecting/amplifying section 16 is converted into a digital signal by an A/D converter 18, and the converted digital signal is thereafter received by the CPU 1. An input section 19 is used to start a pulse wave propagation time calibrating, and input blood pressure values P1, P2 used for a calibration and a threshold _BP that serves as a reference for noninvasive blood pressure re-measurement using the cuff 2, and the like.

The CPU 1 executes a processing program based on the outputs from the A/D converters 7, 11, 17, 18 and the outputs from the input section 19, and displays the results of the processing on a display 22 that is an output means. That is, the CPU 1 controls the discharge valve 3 and the pressure pump 4 at a predetermined time interval, calculates a blood pressure value based on the outputs of the A/D converter 7 at such interval, and displays the result on the display 22. The CPU 1 further calculates a heart rate by receiving A/D converter 11 outputs and displays the result on the display 22 together with an ECG waveform. Still further, the CPU 1 not only calculates the arterial oxygen saturation but also measures a pulse wave by receiving outputs from the A/D converters 17, 18 and displays the respective results on the display 22.

Still further, the CPU 1 counts the pulse wave propagation time from the appearance of the peak value of an R wave of an ECG waveform to the appearance of the bottom value of a pulse wave at the time of making a noninvasive blood pressure measurement using the cuff 2, and calculates a blood pressure value from both the counted time as well as parameters α, β specific to a subject obtained at the time of making a pulse wave propagation time calibration. Then, the CPU 1 computes a difference between the blood pressure value calculated from the pulse wave propagation time and the measured value obtained from the noninvasive blood pressure measurement using the cuff 2, judges whether or not such difference is within a predetermined threshold, and if it is judged that the difference exceeds the threshold, the CPU 1 makes a noninvasive blood pressure measurement again using the cuff 2.

A memory (ROM) 20 connected to the CPU 1 stores the processing program, and a memory (RAM) 21 also connected to the CPU 1 stores processed data.

The cuff 2, the discharge valve 3, the pressure pump 4, the pressure sensor 5, the cuff pressure detecting/amplifying section 6, and the A/D converter 7 constitute the blood pressure measuring means. Further, the RAM 21 corresponds to the threshold storage means. Further, the ECG electrodes 9, the ECG signal detecting/amplifying section 10, and the A/D converter 11 constitute the time interval detection reference point detecting means. Further, the pulse oximeter probe 12, the LED current control sections 13, 14, the photoelectric pulse wave signal detecting/amplifying sections 15, 16, and the A/D converters 17, 18 constitute the pulse wave detecting means. Further, the CPU 1 corresponds to the calculating means and the control means.

B. Operation of the blood pressure monitoring apparatus

Figure 2:
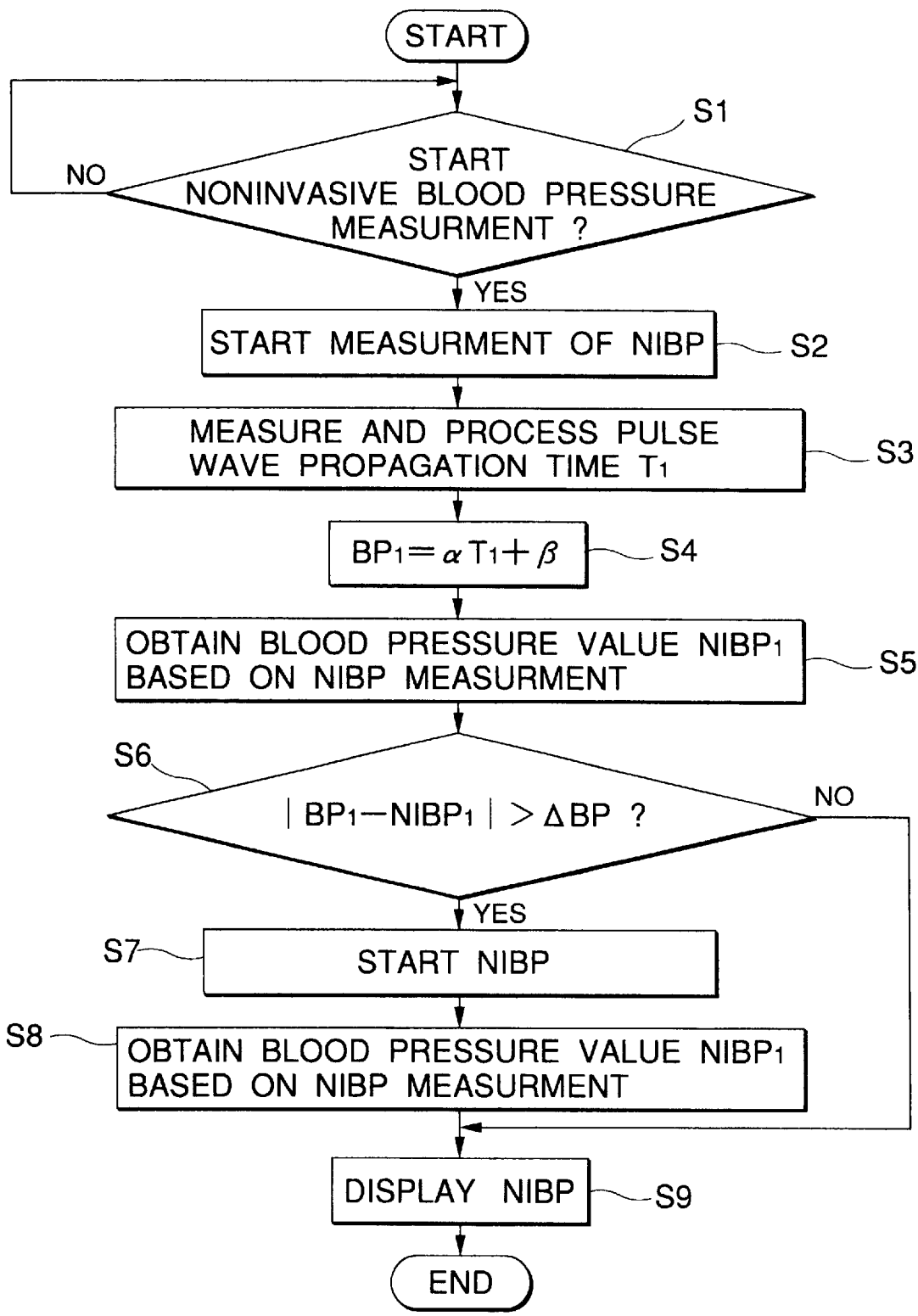
FIG. 2 is a flowchart showing an operation of the blood pressure monitoring apparatus shown in FIG. 1.

An operation of the thus configured blood pressure monitoring apparatus will be described next with reference to the flowchart shown in FIG. 2. In the following description, it is assumed that: a pulse wave propagation time calibration has already been made, so that the parameters α, β specific to a subject have been written to the memory 21; and the threshold _BP that serves as a reference for noninvasive blood pressure re-measurement using the cuff 2 has been written to the memory 21.

First, the CPU 1 judges whether or not it is a timing to start a noninvasive blood pressure measurement using the cuff 2 in Step S1. If the CPU 1 judges that it is not the timing to start a noninvasive blood pressure measurement, the CPU 1 repeats executing this step, whereas if the CPU 1 judges that it is such timing, the CPU 1 advances to Step S2 and starts making a noninvasive blood pressure measurement using the cuff 2. Then, in Step S3, the CPU 1 counts a pulse wave propagation time T1, and writes the result to the memory 21.

After having counted the pulse wave propagation time T1, the CPU 1 calculates a blood pressure value BP1 from the pulse wave propagation time T1 and writes the result to the memory 21 in Step S4. That is, the blood pressure value BP1 is obtained by substituting the pulse wave propagation time T1 and the parameters α, β written in the memory 21 in the following equation.

$$P = \alpha T + \beta$$

After having calculated the blood pressure value BP1 from the pulse wave propagation time T1, the CPU 1 obtains a blood pressure value NIBP1 based on the noninvasive blood pressure measurement using the cuff 2 in Step S5. Then, in Step S6, the CPU 1 obtains a difference between the blood pressure value BP1 and the blood pressure value NIBP1, and judges whether or not the absolute value of the obtained difference exceeds the threshold _BP written in the memory 21. If it is judged that the absolute value of the difference between the blood pressure value BP1 and the blood pressure value NIBP1 exceeds the threshold _BP, the CPU 1 judges that the result of the noninvasive blood pressure measurement using the cuff 2 is abnormal, eliminates the currently measured value, and makes a noninvasive blood pressure measurement using the cuff 2 again in Step S7. When a blood pressure value $NIBP_1'$ is obtained from the re-measurement in Step S8, the CPU 1 displays such blood pressure value NIBP1' on the display 22 in Step S9.

On the other hand, if it is judged that the absolute value of the difference between the blood pressure value BP1 and the blood pressure value NIBP1 does not exceed the threshold _BP in Step S6, the CPU 1, judging that the result of the noninvasive blood pressure measurement using the cuff 2 is normal, displays the blood pressure value NIBP1 in Step S9.

As described above, in this mode of embodiment, a pulse wave propagation time T1 from the appearance of the peak value of an R wave of an ECG waveform to the appearance of the bottom value of a pulse wave is counted at the time of making a noninvasive blood pressure measurement using the cuff 2, and calculates a blood pressure value BP1 from both the counted time T1 and the parameters α, β specific to a subject obtained at the time of making a pulse wave propagation time calibration. Then, an absolute value of a difference between the blood pressure value BP1 and a blood pressure value NIBP1 obtained by the noninvasive blood pressure measurement using the cuff 2 is calculated, and it is judged whether or not such absolute value exceeds a predetermined threshold _BP. If it is judged that such absolute value exceeds the threshold _BP, a noninvasive blood pressure measurement using the cuff 2 is made again, and a blood pressure value NIBP1' obtained as a result of such re-measurement is displayed on the display 22.

Therefore, even if an abnormal value has been found in a noninvasive blood pressure measurement using the cuff 2, such abnormal value is not used in the computation. Therefore, not only a highly reliable measured blood pressure value can be obtained, but also unnecessary alarming can be eliminated and post-measurement analyses will be done substantially smoothly. In addition, when an abnormal value has been found, blood pressure is re-measured automatically. That is, the cumbersome operation of manually re-measuring blood pressure can be dispensed with, which in turn contributes to improving operability.

While whether or not the result of a noninvasive blood pressure measurement using the cuff 2 is normal is judged by judging whether or not a difference between a blood pressure value NIBP1 obtained by the noninvasive blood pressure measurement using the cuff 2 and a blood pressure value BP1 obtained from a pulse wave propagation time T1 exceeds a threshold _BP in the aforementioned mode of embodiment, such judgment may be made from a fluctuating condition observed on a blood pressure value obtained from a noninvasive blood pressure measurement using the cuff 2 and a fluctuation condition observed on a pulse wave propagation time, respectively. For example, the following judging methods may be proposed.

(1) If a noninvasive blood pressure measurement is made using the cuff 2 and not only the blood pressure value obtained from such measurement exceeds a reference but also a pulse wave propagation time also exceeds a reference, then the result of the noninvasive blood pressure measurement is judged to be normal, because both the blood pressure value and the time exceed the references thereof, respectively.

(2) If the result of a noninvasive blood pressure measurement using the cuff 2 fluctuates from the result of a previous noninvasive blood pressure measurement using the cuff 2 although the pulse wave propagation times exhibit almost no fluctuation, then the result of the noninvasive blood pressure measurement is judged to be abnormal.

(3) If the results of noninvasive blood pressure measurements using the cuff 2 do not fluctuate although pulse wave propagation times fluctuate, then the result of the noninvasive blood pressure measurement is judged to be abnormal.

According to the blood pressure monitoring apparatuses of the present invention, even if an abnormal value has been found in a noninvasive blood pressure measurement using the cuff 2, such abnormal value is not used in the computation. Therefore, not only a highly reliable measured blood pressure value can be obtained, but also unnecessary alarming can be eliminated and post-measurement analyses will be done substantially smoothly. In addition, when an abnormal value has been found, blood pressure is re-measured automatically. Therefore, the cumbersome operation of manually starting a re-measurement can be dispensed with, which in turn contributes to improving operability.

What is claimed is:

1. A blood pressure monitoring apparatus comprising:

blood pressure measuring means for measuring blood pressure using a cuff;

time interval detection reference point detecting means for detecting a time interval detection reference point on a pulse wave at an aorta of a body;

pulse wave detecting means for detecting a pulse wave at peripheral blood vessels appearing with a time delay with respect to the pulse wave at the aorta;

pulse wave propagation time counting means for counting a pulse wave propagation time based on detected outputs from the time interval detection reference point detecting means and the pulse wave detecting means; and control means for judging whether or not a blood pressure value measured by the blood pressure measuring means is an abnormal value based on a fluctuating condition observed on the blood pressure value measured by the blood pressure measuring means and a fluctuating condition observed on a pulse wave propagation time counted by the pulse wave propagation time counting means at the time the blood pressure value has been measured, and measuring blood pressure again by controlling the blood pressure measuring means when the blood pressure value has been judged to be an abnormal value.

2. A blood pressure monitoring apparatus comprising:

blood pressure measuring means for measuring blood pressure using a cuff;

threshold storage means for storing a threshold serving as a reference for blood pressure re-measurement using the cuff, the threshold being inputted from an external source;

time interval detection reference point detecting means for detecting a time interval detection reference point on a pulse wave at an aorta of a body;

pulse wave detecting means for detecting a pulse wave at peripheral blood vessels appearing with a time delay with respect to the pulse wave at the aorta;

pulse wave propagation time counting means for counting a pulse wave propagation time based on detected outputs from the time interval detection reference point detecting means and the pulse wave detecting means;

calculating means for calculating a blood pressure value based on a pulse wave propagation time counted by the pulse wave propagation time counting means at the time the blood pressure measurement has been made by the blood pressure measuring means; and control means for judging whether or not an absolute value of a difference between a blood pressure value measured by the blood pressure measuring means and a blood pressure value calculated by the calculating means at the time the blood pressure value has been measured exceeds the threshold stored in the threshold storage means, and measuring blood pressure again by controlling the blood pressure measuring means when the absolute value of the difference has been judged to exceed the threshold.

3. A method for monitoring blood pressure comprising:

measuring blood pressure using a cuff;

detecting a time interval detection reference point on a pulse wave at an aorta of a body;

detecting a pulse wave at peripheral blood vessels appearing with a time delay with respect to the pulse wave at the aorta;

counting a pulse wave propagation time based on detected outputs from the time interval detection reference point and the pulse wave;

judging whether or not a blood pressure value is an abnormal value based on a fluctuating condition observed on the blood pressure value and a fluctuating condition observed on a pulse wave propagation time counted at the time the blood pressure value has been measured; and measuring blood pressure again by controlling the blood pressure measuring means when the blood pressure value has been judged to be an abnormal value.

4. A method for monitoring blood pressure comprising:

measuring blood pressure using a cuff;

storing a threshold serving as a reference for blood pressure re-measurement using the cuff, the threshold being inputted from an external source;

detecting a time interval detection reference point on a pulse wave at an aorta of a body;

detecting a pulse wave at peripheral blood vessels appearing with a time delay with respect to the pulse wave at the aorta;

counting a pulse wave propagation time based on detected outputs from the time interval detection reference point and the pulse wave;

calculating a blood pressure value based on a pulse wave propagation time at the time the blood pressure measurement has been made; and judging whether or not an absolute value of a difference between a blood pressure value and a blood pressure value calculated at the time the blood pressure value has been measured exceeds the threshold stored in the threshold storage means; and measuring blood pressure again when the absolute value of the difference has been judged to exceed the threshold.

* * * * *